(12) United States Patent
Fankhauser et al.

(10) Patent No.: US 9,896,644 B2
(45) Date of Patent: Feb. 20, 2018

(54) POWDERY, MUSKY ODORANT MACROCYCLES

(71) Applicant: Firmenich SA, Geneva (CH)

(72) Inventors: Peter Fankhauser, Meyrin (CH); Fredi Bruhlmann, Geneva (CH); Koenraad Vanhessche, Feigères (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/111,523

(22) PCT Filed: Jan. 12, 2015

(86) PCT No.: PCT/EP2015/050393
§ 371 (c)(1),
(2) Date: Jul. 14, 2016

(87) PCT Pub. No.: WO2015/107017
PCT Pub. Date: Jul. 23, 2015

(65) Prior Publication Data
US 2016/0340606 A1 Nov. 24, 2016

(30) Foreign Application Priority Data

Jan. 14, 2014 (EP) .................................. 14151071
Jul. 2, 2014 (EP) .................................. 14175409

(51) Int. Cl.
*C11B 9/00* (2006.01)
*C11D 3/50* (2006.01)
*A61K 8/35* (2006.01)
*A61Q 13/00* (2006.01)

(52) U.S. Cl.
CPC .............. *C11B 9/0038* (2013.01); *A61K 8/35* (2013.01); *A61Q 13/00* (2013.01); *C11D 3/50* (2013.01)

(58) Field of Classification Search
CPC .................................................. C11B 9/0038
See application file for complete search history.

(56) References Cited

U.S. PATENT DOCUMENTS 3,718,696 A 2/1973 Mookherjee et al.
5,354,735 A * 10/1994 Demole .................. C07C 45/57
424/76.4

FOREIGN PATENT DOCUMENTS

EP 584477 A1 3/1994
EP 1820842 A1 8/2007

OTHER PUBLICATIONS

International Search Report and Written Opinion, application PCT/EP2015/050393 dated Apr. 22, 2015.
Corey et al., Angew. Chem. Int. Ed. 1998, 37, 1986-2012.
Fehr et al., Eur. J. Org. Chem. 2004, 1953-1957.
Fujimoto et al., Biosci. Biotechnol. Biochem., 66(6), 2002, 1389-1392.
Knopff et al., Angew. Chem. Int. Ed. 2007, 46, 1307-1310.
Muller et al., Helv. Chim. Acta 1991, 74, 232-240.
Noyori et al., Angew. Chem. Int. Ed. 2001, 40, 40-73.
Noyori et al., J. Am. Chem. Soc. 1979, 3129-3131.
Robinson et al., Tetrahedron Asymmetry 14, 2003, 1407-1446.
T. Yamada, Synthesis 2008, No. 10, pp. 1628-1640.

* cited by examiner

*Primary Examiner* — Lanee Reuther
(74) *Attorney, Agent, or Firm* — Winston & Strawn LLP

(57) ABSTRACT

The present invention concerns a composition of matter comprising i) from 35 to 55% w/w of (R,Z)-3-methyl-cyclopentadec-5-en-1-one, having an ee of at least 80%; ii) from 27 to 40% of (R,E)-3-methyl-cyclopentadec-5-en-1-one, having an ee of at least 80%; iii) from 3 to 20% of (S,E)-3-methyl-cyclopentadec-4-en-1-one, having an ee of at least 80%; and iv) from 0 to 5% of (S,Z)-3-methyl-cyclopentadec-4-en-1-one, having an ee of at least 80%; as well as the use as perfuming ingredient of said composition of matter.

23 Claims, No Drawings

POWDERY, MUSKY ODORANT MACROCYCLES

This application is a 371 filing of International Patent Application PCT/EP2015/050393 filed 12 Jan. 2015, which claims the benefit of European patent application no 14151071.9 filed 14 Jan. 2014 and European patent application no 14175409.3 filed 2 Jul. 2014.

TECHNICAL FIELD

The present invention relates to the field of perfumery. More particularly, it concerns a composition of matter comprising
i) from 35 to 55% w/w of (R,Z)-3-methyl-cyclopentadec-5-en-1-one, having an ee of at least 80%;
ii) from 27 to 40% of (R,E)-3-methyl-cyclopentadec-5-en-1-one, having an ee of at least 80%;
iii) from 3 to 20% of (S,E)-3-methyl-cyclopentadec-4-en-1-one, having an ee of at least 80%; and
iv) from 0 to 5% of (S,Z)-3-methyl-cyclopentadec-4-en-1-one, having an ee of at least 80%
Said composition of matter is a useful perfumery ingredient, and therefore the present invention comprises the invention compound as part of a perfuming composition or of a perfuming consumer product.

PRIOR ART

Muscenone® (Firmenich SA, Geneva, Switzerland) is well known ingredient used in perfumery. Muscenone is a racemic mixture of various isomers (mainly Z-3-methyl-cyclopentadec-5-en-1-one, E-3-methyl-cyclopentadec-5-en-1-one, E-3-methyl-cyclopentadec-4-en-1-one and Z-3-methyl-cyclopentadec-4-en-1-one) and is reported to possess very elegant nitromusk powdery type of odor reminiscent of Musk ketone (i.e. powdery/musky, nitromusk), with a "slight animal but natural undertone".

In EP 0584477, a remarkable difference between the odors of the 3-methyl-cyclopentadec-(4 or 5)-en-1-one position isomers is noticed. The 3-methyl-cyclopentadec-5-en-1-one exhibits a "very musky, slightly animal note, with a strong nitro-musk character" whereas the 3-methyl-cyclopentadec-4-en-1-one develops a very weak musky odor devoid of character.

The enantioselective synthesis of (3R,5Z)-methyl-cyclopentadecen-1-one and (3S,5Z)-3-methyl-cyclopentadecen-1-one described in *Eur. J. Org. Chem.* 2004, 1953 allowed to demonstrate the influence of the configuration of the methyl group. The R isomer distinguishes itself by an outstandingly low threshold value and a highly desirable nitromusk character. A more detailed olfactory profile of the four isomers of 5-Muscenone® is given in *Biosci. Biotechnol. Biochem.* 2002, 1389 presenting the (3R,5Z)-methyl-cyclopentadec-5-en-1-one as the only isomer having the powdery/musk note, but having also a strong warm, animal character which is overall detrimental when compared to the elegance of Muscenone®.

The powdery/musk note is very appreciated in perfumery and is the one which bring the value to Muscenone®.

Now in view of the importance of such note, there is a marked interest for new perfumery ingredients providing as strong as possible powdery/musk note which leads to the use of less material. We have now unexpectedly discovered a synergic effect between various isomers of 3-methyl-cyclopentadec-(4 or 5)-en-1-one which results in the present composition of matter possessing a stronger powdery character which maintains the roundness and elegance of the overall note, i.e. without an overdue animal character. The prior art does not anticipate that the present composition of matter provided such increase in performance.

DESCRIPTION OF THE INVENTION

We have now surprisingly discovered that a composition of matter comprising from about:
35 to 55% w/w of (R,Z)-3-methyl-cyclopentadec-5-en-1-one, having an ee of at least 80%;
27 to 40% w/w of (R,E)-3-methyl-cyclopentadec-5-en-1-one, having an ee of at least 80%;
3 and 20% w/w of (S,E)-3-methyl-cyclopentadec-4-en-1-one, having an ee of at least 80%; and
0 to 5% w/w of (S,Z)-3-methyl-cyclopentadec-4-en-1-one, having an ee of at least 80%;
the percentage being relative to the total weight of the composition of matter; can be used as perfuming ingredient, for instance to impart odor notes of the powdery, musk type having also a sweet/vanilla aspect.

For the sake of clarity, the expression "ee" stands for "enantiomeric excess" which is defined as the excess of one enantiomer over the other, expressed as a percentage of the whole and calculated as below wherein R and S are the respective fractions of enantiomers in a mixture:

$$ee = ((R-S)/(R+S)) \times 100$$

According to an embodiment of the invention, in the present composition of matter the various constituents mentioned above are present in the following amounts:
38 to 51% w/w of (R,Z)-3-methyl-cyclopentadec-5-en-1-one;
30 to 37% w/w of (R,E)-3-methyl-cyclopentadec-5-en-1-one;
6 and 15% w/w of (S,E)-3-methyl-cyclopentadec-4-en-1-one; and
0 to 2% w/w of (S,Z)-3-methyl-cyclopentadec-4-en-1-one.

According to an embodiment of the invention, in the present composition of matter the various constituents mentioned above are present in the following amounts:
40 to 50% w/w of (R,Z)-3-methyl-cyclopentadec-5-en-1-one;
32 to 36% w/w of (R,E)-3-methyl-cyclopentadec-5-en-1-one;
8 and 14% w/w of (S,E)-3-methyl-cyclopentadec-4-en-1-one; and
0 to 2% w/w of (S,Z)-3-methyl-cyclopentadec-4-en-1-one.

According to any one of the above embodiments of the invention, the present composition of matter may comprise from about 42 to 48% w/w of (R,Z)-3-methyl-cyclopentadec-5-en-1-one.

According to any one of the above embodiments of the invention, the present composition of matter may comprise from about 32 to 36% w/w of (R,E)-3-methyl-cyclopentadec-5-en-1-one.

According to any one of the above embodiments of the invention, the present composition of matter may comprise from about 8 to 14% w/w of (S,E)-3-methyl-cyclopentadec-4-en-1-one.

According to any one of the above embodiments of the invention, the various constituent may be present in specific molar ratio ranges. As non-limiting example, one may cite the following molar ratio (mr) ranges:

(mr) of [(R,Z)-3-methyl-cyclopentadec-5-en-1-one/(R,E)-3-methyl-cyclopentadec-5-en-1-one] being comprised between 1.6 and 1.0, or between 1.5 and 1.1, or even between 1.4 and 1.2; and/or (mr) of [(R,Z)-3-methyl-cyclopentadec-5-en-1-one/(S,E)-3-methyl-cyclopentadec-4-en-1-one] being comprised between 6.0 and 2.5, or even between 4.5 and 3.0.

According to any one of the above embodiments of the invention, each compound specified in the present composition of matter (i.e. (R,Z)-3-methyl-cyclopentadec-5-en-1-one, (R,E)-3-methyl-cyclopentadec-5-en-1-one, (S,E)-3-methyl-cyclopentadec-4-en-1-one and (S,Z)-3-methyl-cyclopentadec-4-en-1-one) may have an ee of at least 85%, 90% or even 95%.

According to a particular embodiment of the invention, the present composition of matter is one comprising from about:

42 to 48% w/w of (R,Z)-3-methyl-cyclopentadec-5-en-1-one, having an ee of at least 90%;
32 to 36% w/w of (R,E)-3-methyl-cyclopentadec-5-en-1-one, having an ee of at least 90%;
8 to 14% w/w of (S,E)-3-methyl-cyclopentadec-4-en-1-one, having an ee of at least 90%; and
0 to 2% w/w of (S,Z)-3-methyl-cyclopentadec-4-en-1-one, having an ee of at least 90%.

As mentioned above, the composition of matter of the invention possesses a strong musk and tenaceous odor with a stronger than expected natural powdery note. The overall profile demonstrates to be of high interest for perfumer since it opens new perspectives to the perfumer's creativity when compared with the prior art racemic or enantiopure analogues.

Indeed, when the odor of the invention's composition of matter is compared with that of the prior art racemic composition of matter (i.e. Muscenone®, then the invention's compositions of matter distinguish themselves by a clearly different odor profile characterized by a stronger powdery, and round note and by much weaker animal note, so characteristic of the prior art compound. The invention's compositions of matter distinguish themselves also by showing a sweet/vanillic aspect. Overall, while the racemic composition of matter is more in the masculine direction due to its animal note, the present composition of matter is more on the feminine direction.

The pure enantiomer analogue (i.e. (3R,5Z)-methyl-cyclopentadec-5-en-1-one) is described in the prior art as being the only isomer having the powdery/musk note, so any composition of matter wherein said isomer is diluted should have a weaker powdery note. However, this is not the case and when the odor of the invention's composition of matter is compared with that of the prior art pure enantiomer (i.e. (3R,5Z)-methyl-cyclopentadec-5-en-1-one), then the invention's compositions of matter demonstrated to have an powdery/musk note as strong as the one of the pure enantiomer, but still the present compositions of matter distinguish themselves by a more equilibrated being clearly less animal, more feminine, sweet, round and elegant.

In other words, the present composition of matter combines the strength of powdery/musk notes of (3R,5Z)-methyl-cyclopentadecen-1-one with the elegance of Muscenone®, thus reaching an optimal perfumistic equilibrium which renders the invention composition of matter different from the prior art composition and/or compound.

Said differences lend the invention's compounds and the prior art compounds to be each suitable for different uses, i.e. to impart different organoleptic impressions.

As mentioned above, the present composition of matter can be used as perfuming ingredient. Therefore another object of the present invention concerns a method to confer, enhance, improve or modify the odor properties of a perfuming composition or of a consumer product, which method comprises adding to said composition or consumer product an effective amount of the invention's composition of matter.

According to a particular embodiment, such method is aimed to boost the musk, powdery, sweet note and the feminine aspect of a perfuming composition or of a consumer product.

The present composition of matter can be advantageously employed as perfuming ingredients in a variety of compositions. Therefore, another object of the present invention is a perfuming composition comprising:

i) as perfuming ingredient, the invention's composition of matter as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or to polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, to etc. A detailed description of the nature and type of adjuvant commonly used in perfuming bases cannot be exhaustive, but it has to be mentioned that said ingredients are well known to a person skilled in the art.

An invention's composition consisting of invention's composition of matter and at least one perfumery carrier represents a particular embodiment of the invention as well as a perfuming composition comprising invention's composition of matter, at least one perfumery carrier, at least one perfumery base, and optionally at least one perfumery adjuvant.

For the sake of clarity, it is also understood that any mixture resulting directly from a chemical synthesis, e.g. a reaction medium without an adequate purification, in which the composition of matter of the invention would be involved as a starting, intermediate or end-product could not be considered as a perfuming composition according to the invention as far as said mixture does not provide the inventive compound in a suitable form for perfumery.

Furthermore, the invention's composition of matter can also be advantageously used in all the fields of modern perfumery, i.e. fine or functional perfumery, to positively impart or modify the odor of a consumer product into which said invention's composition of matter is added. Consequently, another object of the present invention is represented by a perfumery consumer product comprising, as perfuming ingredient, the invention's composition of matter, as defined above.

The invention's composition of matter can be added as such or as part of an invention's perfuming composition.

For the sake of clarity, it has to be mentioned that, by "perfumery consumer product" it is meant a consumer product which is expected to deliver at least a pleasant perfuming effect to the surface to which it is applied (e.g. skin, hair, textile, or home surface). In other words, a perfumery consumer product according to the invention is a perfumed consumer product which comprises the functional formulation, as well as optionally additional benefit agents, corresponding to the desired consumer product, e.g. a detergent or an air freshener, and an olfactive effective amount of at least one invention's composition of matter. For the sake of clarity, said perfuming consumer product is a non-edible product.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer products may represent an aggressive medium for the invention's composition of matter, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the invention's composition of matters according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.1% to 10% by weight, or even more, of the composition of matter of the invention based on the weight of the composition into which they are incorporated. Concentrations lower than these, such as in the order of 0.01% to 5% by weight, can be used when these compositions of matter are incorporated into perfumed articles, percentage being relative to the weight of the article.

The invention's composition of matter can be prepared from a treatment with strong acid of the enantioenriched hydroxy ketone (3R)-5-hydroxy-3-methylcyclopentadecan-1-one or the corresponding enantioenriched enolether (14R)-14-methyl-16-oxabicyclo[10.3.1]hexadec-12-ene according to EP 0584477. In any case the composition of matter can be obtained from 3-methylcyclopentadecane-1,5-dione. In one to case, the enantioenriched enolether can be synthesized according to different methods. One example is described in *Eur. J. Org. Chem.* 2004 1953 wherein the key steps is a intramolecular aldol condensation of the readily available 3-methylcyclopentadecane-1,5-dione (*Helv. Chim. Acta.* 1967, 50, 705) following by the kinetic resolution using Corey's oxazaborolidine and an Eschenmoser fragmentation. The aldol condensation and kinetic resolution could be substituted by an enantioselective intramolecular aldol condensation as reported in *Angew. Chem. Int. Ed.* 2007, 1307. An alternative to synthesis the enantioenriched enolether is an enantioselective mono reduction of 3-methylcyclopentadecane-1,5-dione. As not limiting examples, one can cite transition metal mediated desymmetrization using Noyori's asymmetric transfer hydrogenation catalyst (*Tetrahedron: Asymmetry* 2003, 1407) or Noyori's hydrogenation catalyst (*Angew. Chem. Int. Ed.* 2001, 40). Iridium-Catalyzed Transfer Hydrogenation of Ketones is a possible alternative (*Helv. Chim. Acta* 1991, 74, 232). Oxazaborolidine-catalyst is also well known to perform this kind of reduction (*Angew. Chem. Int. Ed.* 1998, 1986). The enantioselective borohydride reduction of carbonyl compounds could be also performed in the presence of a catalytic amount of an optically active cobalt (II) complex (*Synthesis* 2008, 1628). Modified metal hydride reagent with optically active ligand could lead to the desired chiral hydroxyketone (*J. Am. Chem. Soc.* 1979, 3129). In second case, enzymatic method could also be considered for the enantioselective mono reduction of 3-methylcyclopentadecane-1,5-dione. The skilled person in the art will be able to select the suitable enzyme by standard screening method of library of known enzymes as baker'yeast, alcohol dehydrogenase or ketoreductase.

In any case, the chiral reaction mixture accessible via the methodologies mentioned above contains various proportions of (14R)-14-methyl-16-oxabicyclo[10.3.1]hexadec-12-ene and (3R)-5-hydroxy-3-methylcyclopentadecan-1-one. The reaction is preferably performed to lead to partial conversion, in order to avoid subsequent diol formation. Therefore the reaction mixture could contain also some remaining 3-methylcyclopentadecane-1,5-dione. This mixture can be separated into the individual ingredients, or submitted as such to the acid treatment below, yielding the composition of matter.

A preferred way of proceeding consists in a thermal and/or acid treatment followed by purification of the resulting reaction mixture in order to convert (3R)-5-hydroxy-3-methylcyclopentadecan-1-one into the corresponding enolether. The to subsequent distillation allows the recovery of possibly present higher boiling 3-methylcyclopentadecane-1,5-dione, in order to recycle it into the process.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of Composition of Matter

Distilled (14R)-14-methyl-16-oxabicyclo[10.3.1]hexadec-12-ene (88% pure; 46.5 g; 0.173 mol) containing 3% residual 3-methylcyclopentadecane-1,5-dione was dissolved in toluene (60 g). Phosphoric acid (85% aq; 35.0 g; 0.304 mol) was added and the heterogeneous mixture heated to 100° C. under vigorous stirring. The reaction progress was monitored by GC. In order to reliably dose thermally labile (3R)-5-hydroxy-3-methylcyclopentadecan-1-one, samples were derivatized (excess MSTFA, 80° C., 30 min; conversion of (3R)-5-hydroxy-3-methylcyclopentadecan-1-one to the corresponding TMS ether) prior to GC injection. After 4 hours, the mixture was cooled to 50° C. and the lower phase decanted (34.4 g, recovered aq. H$_3$PO$_4$). This aqueous phase was extracted with MTBE (2×50 ml). The pooled organic phases were washed with 5% aq. NaHCO$_3$ (40 g) and a saturated solution of NaCl (50 g), dried (Na$_2$SO$_4$) and concentrated under vacuum to give the crude compound (42.2 g).

Bulb-to-bulb distillation (115-120° C. oven temperature, 0.1 mbar) afforded a colorless oil (39.6 g, 75.4% yield). Vacuum distillation (Widmer column) gave the target mixture (bp 90° C./0.05 mbar) having the following isomer composition: 44% (R,Z)-3-methyl-cyclopentadec-5-en-1-one, 34% (R,E)-3-methyl-cyclopentadec-5-en-1-one, 12% (S,E)-3-methyl-cyclopentadec-4-en-1-one, and 1% (S,Z)-3-methyl-cyclopentadec-4-en-1-one. [α]$D_{20}$ (CH$_3$OH, c=2.84)+2.32. This corresponds to an enantiomer excess (ee) of 90%. The ee was measured employing the following procedure: a sample of above mixture was converted into muscone (5% Pd/C/H$_2$, ethyl acetate, 25° C.). Analysis by GC using a ChirasilDex CB (Chrompack) chiral column (chemically bonded beta cyclodextrin permethylether, 25 m, 0.25 μm) had allowed determination of the ee. The order of elution from this column is: (R)-(−)-muscone, (S)-(+)-muscone.

Example 2

Preparation of a Perfuming Composition

A perfuming composition for fine fragrance, of the powdery/floral type, was prepared by admixing the following ingredients:

| Parts by weight | Ingredient |
| --- | --- |
| 50 | Benzyl Acetate |
| 30 | 10%*Cis-3-Hexenol Acetate |
| 20 | Citronellyle Acetate |
| 10 | Geranyl Acetate Extra |
| 30 | Hexyl Acetate |
| 40 | Isoeugenyl Acetate |
| 100 | Hexylcinnamic Aldehyde |
| 40 | 10%* Allyl Amyl Glycolate |
| 300 | Bergamote Abergapt |
| 50 | 10%* Cascalone ™[1)] |
| 80 | Cashmeran[2)] |
| 200 | Cedarwood Oil |
| 70 | Cetalox ®[3)] |
| 50 | 10%* Cis-3-Hexenol |
| 50 | Citronellol |
| 800 | Coranol[4)] |
| 10 | Cyclogalbanate[5)] |
| 20 | Cyclosal |
| 80 | 10%* Damascenone |
| 150 | Dihydromyrcenol[6)] |
| 80 | Ethylvanilline |
| 200 | Exaltolide ®[7)] |
| 50 | 2-methyl-4-(2,2,3-trimethyl-3-cyclopenten-1-yl)-4-penten-1-ol |
| 300 | Florol ®[8)] |
| 80 | 3-(4-methoxyphenyl)-2-methylpropanal |
| 100 | Gamma Decalactone |
| 100 | Gamma Undecalactone |
| 150 | Geraniol 60 |
| 1750 | Hedione ®[9)] |
| 300 | Heliopropanal[10)] |
| 200 | Helvetolide ®[11)] |
| 300 | Hydroxycitronellal |
| 20 | 10%* 1-Phenylvinyl acetate |
| 250 | Ionone Beta |
| 1000 | Iso E Super[12)] |
| 50 | 10%* Jasminlactone |
| 300 | Lilial ®[13)] |
| 200 | Linalol |
| 70 | Mandarine |
| 30 | 10%* 2,6-dimethyl-5-heptanal |
| 40 | Methyl Pamplemousse[14)] |
| 300 | Methylionone Alpha Iso |

-continued

| Parts by weight | Ingredient |
|---|---|
| 100 | Muscone |
| 10 | Myrrhone ®[15] |
| 20 | 10%* Neobutenone ® Alpha[16] |
| 50 | 10%* (Z)-1-[(E)-2-butenyloxy]-3-hexene |
| 20 | Patchouli oil |
| 200 | Phenylhexanol |
| 50 | Polysantol ®[17] |
| 200 | Orange Essential Oil |
| 300 | Benzyle Ethyl Salicylate |
| 250 | Cis-3-Hexenol Salicylate |
| 200 | Sclareolate ®[18] |
| 150 | Cis-3-Hexenyl Cis-3-Hexenoate |
| 9600 | |

*in dipropyleneglycol
[1] 7-isopropyl-2H,4H-1,5-benzodioxepin-3-one; origin: Firmenich SA, Geneva, Switzerland
[2] 1,2,3,5,6,7-hexahydro-1,1,2,3,3-pentamethyl-4-indenone; origin: International Flavors & Fragrances, USA
[3] dodecahydro-3a,6,6,9a-tetramethyl-naphtho[2,1-b]furan; origin: Firmenich SA, Geneva, Switzerland
[4] 4-cyclohexyl-2-methyl-2-butanol; origin: Firmenich SA, Geneva, Switzerland
[5] allyle (cyclohexyloxy)-acetate; origin: Symrise, Holzminden, Allemagne
[6] 2,6-dimethyl-7-octen-2-ol; origin: International Flavors & Fragrances, USA
[7] pentadecanolide; origin: Firmenich SA, Geneva, Switzerland
[8] tetrahydro-2-isobutyl-4-methyl-4(2H)-pyranol; origin: Firmenich SA, Geneva, Switzerland
[9] methyl dihydrojasmonate; origin: Firmenich SA, Geneva, Switzerland
[10] 3-(1,3-benzodioxol-5-yl)-2-methylpropanal; origin: Firmenich SA, Geneva, Switzerland
[11] (1S,1'R)-2-[1-(3',3'-dimethyl-1'-cyclohexyl)ethoxy]-2-methylpropyl propanoate; origin: Firmenich SA, Geneva, Switzerland
[12] 1-(octahydro-2,3,8,8-tetramethyl-2-naphthalenyl)-1-ethanone; origin: International Flavors & Fragrances, USA
[13] 3-(4-tert-butylphenyl)-2-methylpropanal; origin: Givaudan SA, Vernier, Switzerland
[14] 6,6-dimethoxy-2,5,5-trimethyl-2-hexene; origin: Givaudan SA, Vernier, Switzerland
[15] 4-(2,2,c-3,t-6-tetramethyl-R-1-cyclohexyl)-3-buten-2-one; origin: Firmenich SA, Geneva, Switzerland
[16] 1-(5,5-dimethyl-1-cyclohexen-1-yl)-4-penten-1-one; origin: Firmenich SA, Geneva, Switzerland
[17] 3,3-dimethyl-5-(2,2,3-trimethyl-3-cyclopenten-1-yl)-4-penten-2-ol; origin: Firmenich SA, Geneva, Switzerland
[18] propyl (S)-2-(1,1-dimethylpropoxy)propanoate; origin: Firmenich SA, Geneva, Switzerland The addition of 400 parts by weight of the composition of matter described in Example 1 to the above-described feminine fragrance composition imparted to the latter a musky character with a strong powdery character as well as and rising and elegant note.

The addition of the same amount of the racemic Muscenone® imparted a similar effect but much less powdery and more animal, less rising.

The addition of the same amount of (3R,5Z)-3-methyl-cyclopentadecen-1-one provided a totally different results with a musk/powdery character of similar amplitude but more masculine, and clearly animal.

Example 3

Preparation of a Perfuming Composition

A perfuming composition for fine fragrance, of musky/fruity type, was prepared by admixing the following ingredients:

| Parts by weight | Ingredient |
|---|---|
| 160 | Benzyl Acetate |
| 80 | Benzyl dimethyl carbinol |
| 40 | 1%* Cis-3-Hexenol Acetate |
| 500 | Hexylcinnamic Aldehyde |
| 40 | Ambrox ® DL[1] |
| 160 | 10%* Cascalone ™[2] |
| 80 | Cassis Base[3] |
| 160 | Raspberry ketone |
| 100 | Citronellol |
| 280 | Coranol[4] |
| 20 | Allyl Cyclohexylpropionate |
| 80 | 10%* Damascenone |
| 160 | (1'R,E)-2-ethyl-4-(2',2',3'-trimethyl-3'-cyclopenten-1'-yl)-2-buten-1-ol |
| 40 | Decal |
| 360 | Dihydromyrcenol[5] |
| 160 | 10%* Ethylpraline |
| 40 | 10%* Gamma Damascone |
| 20 | Gamma Nonalactone |
| 20 | Gamma Undecalactone |
| 80 | Granny Smith[3] |
| 60 | Heliopropanal[6] |
| 100 | Helvetolide ®[7] |
| 60 | Allyle Heptanoate |
| 40 | Hivernal ® Neo[8] |
| 20 | Methyl Jasmonate |
| 260 | Lilial ®[9] |
| 800 | Linalol |
| 300 | Magnolan[10] |
| 100 | Mandarine |
| 20 | 10%* 2,6-dimethyl-5-heptanal |
| 100 | 10%* Crystal moss |
| 2600 | Hedione ®[11] |
| 80 | 10%* (Z)-1-[(E)-2-butenyloxy]-3-hexene |
| 20 | 10%* Rose Oxide |
| 160 | 10%* Cis-3-Hexenol Dist |
| 60 | Orange Essential Oil |
| 60 | Benzyl Propionate |
| 600 | Romandolide ®[12] |
| 200 | Cis-3-Hexenol Salicylate |
| 240 | 3-methyl-5-(2,2,3-trimethyl-3-cyclopenten-1-yl)-2-pentanol |
| 60 | Undecavertol ®[13] |
| 280 | Verdox ®[14] |
| 100 | Ionone Beta |
| 100 | 10%* 2,4-Dimethyl-3-cyclohexene-1-carbaldehyde |
| 9000 | |

*in dipropyleneglycol
[1] (−)-(8R)-8,12-epoxy-13,14,15,16-tetranorlabdane; origin: Firmenich SA, Geneva, Switzerland
[2] 7-isopropyl-2H,4H-1,5-benzodioxepin-3-one; origin: Firmenich SA, Geneva, Switzerland
[3] compounded perfumery basis; origin: Firmenich SA, Geneva, Switzerland
[4] 4-cyclohexyl-2-methyl-2-butanol; origin: Firmenich SA, Geneva, Switzerland
[5] 2,6-dimethyl-7-octen-2-ol; origin: International Flavors & Fragrances, USA
[6] 3-(1,3-benzodioxol-5-yl)-2-methylpropanal; origin: Firmenich SA, Geneva, Switzerland
[7] (1S,1'R)-[1-(3',3'-dimethyl-1'-cyclohexyl)ethoxycarbonyl]methyl propanoate; origin: Firmenich SA, Geneva, Switzerland
[8] 3-(3,3/1,1-dimethyl-5-indanyl)propanal; origin: Firmenich SA, Geneva, Switzerland
[9] 3-(4-tert-butylphenyl)-2-methylpropanal; origin: Givaudan SA, Vernier, Switzerland
[10] 2,4-dimethyl-4,4a,5,9b-tetrahydroindeno[1,2-d][1,3]dioxine; origin: Symrise, Holzminden, Allemagne
[11] methyl dihydrojasmonate; origin: Firmenich SA, Geneva, Switzerland
[12] (1S,1'R)-[1-(3',3'-dimethyl-1'-cyclohexyl)ethoxycarbonyl]methyl propanoate; origin: Firmenich SA, Geneva, Switzerland
[13] 4-methyl-3-decen-5-ol; origin: Givaudan SA, Vernier, Switzerland
[14] 2-tert-butyl-1-cyclohexyl acetate; origin: International Flavors & Fragrances, USA The addition of 100 parts by weight of the composition of matter described in Example 1 to the above-described floral/fruity composition imparted to the latter a reinforced sweet, vanilla connotation with an exaltation of the musk and powdery aspect.

The addition of the same amount of the racemic Muscenone® imparted a totally different result which was less sweet more animal and with a classical musk note.

The addition of the same amount of the (3R,5Z)-3-methyl-cyclopentadecen-1-one, overwritten the whole fragrance by its strong animal note.

Example 4

Preparation of a Perfuming Composition

A perfuming composition for liquid detergent, was prepared by admixing the following ingredients:

| Parts by weight | Ingredient |
|---|---|
| 20 | Amyl Acetate |
| 40 | Hexyl Acetate |
| 100 | Phenylethyl Acetate |
| 100 | StyrallyleAcetate |
| 50 | Aldehyde C 10 |
| 400 | Aldehyde Hexylcinnamic |
| 50 | Aldehyde Supra |
| 40 | Allyl Amyl Glycolate |
| 80 | Ethyl 2-methyl-pentanoate |
| 200 | Benzylacetone |
| 300 | Bergamote oil |
| 20 | Cascalone ™ [1] |
| 50 | Cetalox ® [2] |
| 10 | Rasberry ketone |
| 50 | Cetyver |
| 250 | Citron |
| 150 | Citronellol |
| 500 | Coranol [3] |
| 100 | Cis-2-pentyl-1-cyclopentanol |
| 50 | Damascenone |
| 200 | Damascone Alpha |
| 500 | Dihydromyrcenol |
| 10 | Ethylvanilline |
| 400 | Exaltolide ® Total [4] |
| 300 | Florol ® [5] |
| 50 | Galbex ® [6] |
| 30 | Gamma Undecalactone |
| 100 | Geraniol |
| 400 | Habanolide ® [7] |
| 200 | Heliopropanal [8] |
| 100 | Heliotropine [9] |
| 100 | Helvetolide ® [10] |
| 100 | Hivernal ® [11] |
| 100 | 10%* Methyl Jasmonate |
| 50 | Lemonile ® [12] |
| 50 | Lime oil |
| 400 | Linalol |
| 10 | 2,6-dimethyl-5-heptanal |
| 50 | 2-Ethyl Methylbutyrate |
| 50 | 10%* Trans-2-Hexenal |
| 1500 | Hedione ® [13] |
| 10 | Isojasmone |
| 20 | (Z)-1-[(E)-2-butenyloxy]-3-hexene |
| 40 | Cis-3-Hexenol Dist |
| 300 | Orange Essential Oil |
| 200 | Verdyl Propionate |
| 300 | Romandolide ® [14] |
| 100 | Cis-3-Hexenol Salicylate |
| 300 | Salicynile |
| 300 | Sclareolate ® [15] |
| 50 | Tamarine Base [6] |
| 200 | Terpineol |
| 100 | 3-(4,4-dimethyl-1-cyclohexen-1-yl)propanal |
| 20 | Vanilline Perf |
| 300 | Verdox ® [16] |
| 250 | (+)-(1S,2S,3S)-2,6,6-trimethyl-bicyclo[3.1.1]heptane-3-spiro-2'-cyclohexen-4'-one |
| 50 | 2,4-Dimethyl-3-cyclohexene-1-carbaldehyde |
| 9800 | |

*in dipropyleneglycol
[1] 7-isopropyl-2H,4H-1,5-benzodioxepin-3-one; origin: Firmenich SA, Geneva, Switzerland
[2] dodecahydro-3a,6,6,9a-tetramethyl-naphtho[2,1-b]furan; origin: Firmenich SA, Geneva, Switzerland
[3] 4-cyclohexyl-2-methyl-2-butanol; origin: Firmenich SA, Geneva, Switzerland
[4] pentadecanolide; origin: Firmenich SA, Geneva, Switzerland
[5] tetrahydro-2-isobutyl-4-methyl-4(2H)-pyranol; origin: Firmenich SA, Geneva, Switzerland
[6] compounded perfumery basis; origin: Firmenich SA, Geneva, Switzerland
[7] pentadecenolide; origin: Firmenich SA, Geneva, Switzerland
[8] 3-(1,3-benzodioxol-5-yl)-2-methylpropanal; origin: Firmenich SA, Geneva, Switzerland
[9] 1,3-benzodioxole-5-carbaldehyde; origin: Firmenich SA, Geneva, Switzerland
[10] (1S,1'R)-2-[1-(3',3'-dimethyl-1'-cyclohexyl)ethoxy]-2-methylpropyl propanoate; origin: Firmenich SA, Geneva, Switzerland
[11] 3-(3,3/1,1-dimethyl-5-indanyl)propanal; origin: Firmenich SA, Geneva, Switzerland
[12] 3,7-dimethyl-2/3,6-nonadienenitrile; origin: Givaudan SA, Vernier, Switzerland
[13] methyl dihydrojasmonate; origin: Firmenich SA, Geneva, Switzerland
[14] (1S,1'R)-[1-(3',3'-dimethyl-1'-cyclohexyl)ethoxycarbonyl]methyl propanoate origin: Firmenich SA, Geneva, Switzerland
[15] propyl (S)-2-(1,1-dimethylpropoxy)propanoate; origin: Firmenich SA, Geneva, Switzerland
[16] 2-tert-butyl-1-cyclohexyl acetate; origin: International Flavors & Fragrances, USA The addition of 200 parts by weight of the composition of matter described in Example 1 to the above-described composition imparted to the latter a reinforced round, fresh and "feminine" connotation, reinforcing the aldehydic aspect of the original composition.

The addition of the same amount of the racemic Muscenone® imparted a less sophisticated effect.

What is claimed is:

1. A composition of matter to confer, enhance, improve or modify odor properties of a perfuming composition, consumer product or perfumed article, comprising:
   35 to 55% w/w of (R,Z)-3-methyl-cyclopentadec-5-en-1-one, having an ee of at least 80%;
   27 to 40% w/w of (R,E)-3-methyl-cyclopentadec-5-en-1-one, having an ee of at least 80%;
   3 to 20% w/w of (S,E)-3-methyl-cyclopentadec-4-en-1-one, having an ee of at least 80%; and
   0 to 5% w/w of (S,Z)-3-methyl-cyclopentadec-4-en-1-one, having an ee of at least 80%;
   wherein the % w/w is based on a total weight of the composition of matter;
   and wherein a molar ratio range of [(R,Z)-3-methyl-cyclopentadec-5-en-1-one/(R,E)-3-methyl-cyclopentadec-5-en-1-one] is either (A) between 1.6 and 1.0, (B) between 1.5 and 1.1, or (C) between 1.4 and 1.2.

2. A composition of matter according to claim 1, wherein said composition comprises:
   38 to 51% w/w of (R,Z)-3-methyl-cyclopentadec-5-en-1-one, having an ee of at least 90%;
   30 to 37% w/w of (R,E)-3-methyl-cyclopentadec-5-en-1-one, having an ee of at least 90%;
   6 to 15% w/w of (S,E)-3-methyl-cyclopentadec-4-en-1-one, having an ee of at least 90%; and
   0 to 2% w/w of (S,Z)-3-methyl-cyclopentadec-4-en-1-one, having an ee of at least 90%.

3. A composition of matter according to claim 1, wherein said composition comprises:
   42 to 48% w/w of (R,Z)-3-methyl-cyclopentadec-5-en-1-one, having an ee of at least 90%;
   32 to 36% w/w of (R,E)-3-methyl-cyclopentadec-5-en-1-one, having an ee of at least 90%;
   8 to 14% w/w of (S,E)-3-methyl-cyclopentadec-4-en-1-one, having an ee of at least 90%; and
   0 to 2% w/w of (S,Z)-3-methyl-cyclopentadec-4-en-1-one, having an ee of at least 90%.

4. A composition, of matter to confer, enhance, improve or modify odor properties of a perfuming composition, consumer product or perfumed article, comprising:
   35 to 55% w/w of (R,Z)-3-methyl-cyclopentadec-5-en-1-one, having an ee of at least 80%;
   27 to 40% w/w of (R,E)-3-methyl-cyclopentadec-5-1-one, having an ee of at least 80%;
   3 to 20% w/w of (S,E)-3-methyl-cyclopentadec-4-en-1-one, having an ee of at least 80%; and 0 to 5% w/w of (S,Z)-3-methyl-cyclopentadec-4-en-1-one, having an ee of at least 80% wherein the % w/w is based on a total weight of the composition of matter; and wherein a molar ratio range of [(R,Z)-3-methyl-cyclopentadec-5-en-1-one/(S,E)-3-methyl-cyclopentadec-4-en-1-one] is either (A) between 6.0 and 2.5, or (B) between 4.5 and 3.0.

5. A method to confer, enhance, improve or modify odor properties of a perfuming composition, consumer product or perfumed article, which method comprises adding to said perfuming composition, consumer product or perfumed article an effective amount of a composition of matter comprising:

35 to 55% w/w of (R,Z)-3-methyl-cyclopentadec-5-en-1-one, having an ee of at least 80%;
27 to 40% w/w of (R,E)-3-methyl-cyclopentadec-5-en-1-one, having an ee of at least 80%;
3 to 20% w/w of (S,E)-3-methyl-cyclopentadec-4-en-1-one, having an ee of at least 80%; and
0 to 5% w/w of (S,Z)-3-methyl-cyclopentadec-4-en-1-one, having an ee of at least 80%;
wherein the % w/w is based on a total weight of the composition of matter; and
wherein a molar ratio range of [(R,Z)-3-methyl-cyclopentadec-5-en-1-one/(R,E)-3-methyl-cyclopentadec-5-en-1-one] is either (A) between 1.6 and 1.0, (B) between 1.5 and 1.1, or (C) between 1.4 and 1.2.

6. The method according to claim 5, wherein the composition of matter boosts musk, powdery, sweet note and feminine aspects of the perfuming composition, consumer product, or perfumed article.

7. A perfuming composition comprising
i) the composition of matter, as defined in claim 5;
ii) at least one ingredient selected from the group consisting of a perfumery carrier and a perfumery base; and
iii) optionally at least one perfumery adjuvant.

8. A perfumery consumer product comprising the composition of matter, as defined in claim 5.

9. A perfumery consumer product according to claim 8, characterized in that the perfumery consumer product is a perfume, a fabric care product, a body-care product, an air care product or a home care product.

10. A perfumery consumer product according to claim 8, characterized in that the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

11. A method to confer, enhance, improve or modify odor properties of a perfuming composition, consumer product or perfumed article, which method comprises adding to said perfuming composition, consumer product or perfumed article an effective amount of a composition of matter according to claim 5, wherein the composition comprises:

38 to 51% w/w of (R,Z)-3-methyl-cyclopentadec-5-en-1-one, having an ee of at least 90%;
30 to 37% w/w of (R,E)-3-methyl-cyclopentadec-5-en-1-one, having an ee of at least 90%;
6 to 15% w/w of (S,E)-3-methyl-cyclopentadec-4-en-1-one, having an ee of at least 90%; and
0 to 2% w/w of (S,Z)-3-methyl-cyclopentadec-4-en-1-one, having an ee of at least 90%.

12. The method according to claim 11, characterized in that it boosts the musk, powdery, sweet note and feminine aspects.

13. A perfuming composition comprising
i) the composition of matter, as defined in claim 11;
ii) at least one ingredient selected from the group consisting of a perfumery carrier and a perfumery base; and
iii) optionally at least one perfumery adjuvant.

14. A perfumery consumer product comprising the composition of matter, as defined in claim 11.

15. A perfumery consumer product according to claim 14, characterized in that the perfumery consumer product is a perfume, a fabric care product, a body-care product, an air care product or a home care product.

16. A perfumery consumer product according to claim 14, characterized in that the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

17. A method to confer, enhance, improve or modify the odor properties of a perfuming composition or of a perfumed article, which method comprises adding to said composition or consumer product an effective amount of a composition of matter according to claim 5, wherein the composition comprises:

42 to 48% w/w of (R,Z)-3-methyl-cyclopentadec-5-en-1-one, having an ee of at least 90%;
32 to 36% w/w of (R,E)-3-methyl-cyclopentadec-5-en-1-one, having an ee of at least 90%;
8 to 14% w/w of (S,E)-3-methyl-cyclopentadec-4-en-1-one, having an ee of at least 90%; and
0 to 2% w/w of (S,Z)-3-methyl-cyclopentadec-4-en-1-one, having an ee of at least 90%.

18. The method according to claim 17, characterized in that it boosts the musk, powdery, sweet note and feminine aspects.

19. A perfuming composition comprising
i) the composition of matter, as defined in claim 17;
ii) at least one ingredient selected from the group consisting of a perfumery carrier and a perfumery base; and
iv) optionally at least one perfumery adjuvant.

20. A perfumery consumer product comprising the composition of matter, as defined in claim 17.

21. A perfumery consumer product according to claim 20, characterized in that the perfumery consumer product is a perfume, a fabric care product, a body-care product, an air care product or a home care product.

22. A perfumery consumer product according to claim 20, characterized in that the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

23. A method to confer, enhance, improve or modify odor properties of a perfuming composition, consumer product or perfumed article, which method comprises adding to said perfuming composition, consumer product or perfumed article an effective amount of a composition of matter comprising:
- 35 to 55% w/w of (R,Z)-3-methyl-cyclopentadec-5-en-1-one, having an ee of at least 80%;
- 27 to 40% w/w of (R,E)-3-methyl-cyclopentadec-5-en-1-one, having an ee of at least 80%;
- 3 to 20% w/w of (S,E)-3-methyl-cyclopentadec-4-en-1-one, having an ee of at least 80%;
- 0 to 5% w/w of (S,Z)-3-methyl-cyclopentadec-4-en-1-one, having an ee of at least 80% wherein the % w/w is based on a total weight of the composition of matter; and wherein a molar ratio range of [(R,Z)-3-methyl-cyclopentadec-5-en-1-one/(S,E)-3-methyl-cyclopentadec-4-en-1-one] is either (A) between 6.0 and 2.5, or (B) between 4.5 and 3.0.

* * * * *

UNITED STATES PATENT AND TRADEMARK OFFICE
CERTIFICATE OF CORRECTION

PATENT NO. : 9,896,644 B2
APPLICATION NO. : 15/111523
DATED : February 20, 2018
INVENTOR(S) : Fankhauser et al.

It is certified that error appears in the above-identified patent and that said Letters Patent is hereby corrected as shown below:

In the Claims

Column 12:
Line 64 (Claim 4, Line 6), delete "(R,E)-3methyl-cyclopentadec-5-1-" and insert
-- (R,E)-3-methyl-cyclopentadec-5-en-1- --.

Column 13:
Lines 1-4 (Claim 4, continued), delete "0 to 5% w/w of (S,Z)-3-methyl-cyclopentadec-4-en-1-one, having an ee of at least 80% wherein the % w/w is based on a total weight of the composition of matter; and" and insert the following:
-- 0 to 5% w/w of (S,Z)-3-methyl-cyclopentadec-4-en-1-one, having an ee of at least 80%; wherein the % w/w is based on a total weight of the composition of matter; and --.

Column 14:
Line 4 (Claim 12, Line 2), before "musk," delete "the".
Line 29 (Claim 17, Line 1), after "improve or modify", delete "the".
Line 44 (Claim 18, Line 2), before "musk," delete "the".

Column 15:
Lines 13-16 (Claim 23, Lines 13-16), delete "0 to 5% w/w of (S,Z)-3-methyl-cyclopentadec-4-en-1-one, having an ee of at least 80% wherein the % w/w is based on a total weight of the composition of matter; and" and insert the following:
-- 0 to 5% w/w of (S,Z)-3-methyl-cyclopentadec-en-1-one, having an ee of at least 80%; wherein the % w/w is based on a total weight of the composition of matter; and --.

Signed and Sealed this
Eighth Day of May, 2018

Andrei Iancu
*Director of the United States Patent and Trademark Office*